United States Patent
Lardy et al.

(10) Patent No.: US 6,372,732 B1
(45) Date of Patent: Apr. 16, 2002

(54) USE OF DELTA5-ANDROSTENE-3BETA-OL-7,17-DIONE IN THE TREATMENT OF LUPUS ERYTHEMATOSUS

(75) Inventors: Henry A. Lardy, Madison, WI (US); Charles E. Weeks, Battle Creek, MI (US)

(73) Assignee: Humanetics Corporation, Chanhassen, MN (US)

( * ) Notice: Subject to any disclaimer, the term of this patent is extended or adjusted under 35 U.S.C. 154(b) by 0 days.

(21) Appl. No.: 09/554,952

(22) PCT Filed: Nov. 3, 1998

(86) PCT No.: PCT/US98/23386

§ 371 Date: Dec. 4, 2000

§ 102(e) Date: Dec. 4, 2000

(87) PCT Pub. No.: WO99/25333

PCT Pub. Date: May 27, 1999

Related U.S. Application Data

(60) Provisional application No. 60/066,198, filed on Nov. 19, 1997.

(51) Int. Cl.⁷ ............................................. A61K 31/56
(52) U.S. Cl. ..................... 514/169; 514/177; 514/178; 514/179; 514/182; 514/885
(58) Field of Search ................................ 514/169, 177, 514/178, 179, 182, 885

(56) References Cited

U.S. PATENT DOCUMENTS

| | | | | |
|---|---|---|---|---|
| 5,292,730 A | * | 3/1994 | Lardy | 514/171 |
| 5,296,481 A | * | 3/1994 | Partridge et al. | 514/178 |
| 5,567,696 A | * | 10/1996 | McGuire et al. | 514/170 |
| 5,585,371 A | * | 12/1996 | Lardy | 514/171 |

OTHER PUBLICATIONS

Mitchell, Eddie E., "Addressing the regio– and stereo–selectivity seen in P4502A5 mutants with DHEA", dissertation in partial fulfillment of the requirements of the degree of Doctor of Philosophy at the University of Kentucky, Lexington, Kentucky (1996).

Su, Ching–Yuan "Induction of hepatic mitochondrial glycerophosphate dehydrogenase and malic enzyme 1. Effects of Dehydroepiandrosterone 2. Effects of dehydroepiandrosterone–related steroids and cytochrome P–450 inducers", thesis submitted in partial fulfillment of the requirements of the degree of Doctor of Philosophy, University of Wisconsin–Madison, Madison Wisconsin (1988).

Padgett, David Andrew, "Regulation of the immune system and its response to infection with dehydroepiandrosterone, androstenediol, and androstenetriol", dissertation submitted in partial fulfillment of the requirements for the degree of Doctor of Philosophy at Virginia Commonwealth University, Richmond, Virginia (1994).

Whitcomb, Jeannette Marie, "Effects of dehydroepiandrosterone, DHEA–analogs and food restriction on free radical and autoimmunity in the MRL/1pr mouse", dissertation in partial fulfillment of the requirements of the degree of Doctor of Philosophy, Temple University, Ann Arbor, Michigan (1988).

* cited by examiner

*Primary Examiner*—Frederick Krass

(57) ABSTRACT

Lupus erythematosus can be treated by administering therapeutic amounts of delta-5-androstene-3-beta-ol-7,17-dione and its metabolizable precursors, which are not appreciably metabolized in vivo to androgens, estrogens or dehydroepiandrosterone. Such treatment can be prophylactic, ameliorative or curative in nature.

26 Claims, No Drawings

USE OF DELTA5-ANDROSTENE-3BETA-OL-7, 17-DIONE IN THE TREATMENT OF LUPUS ERYTHEMATOSUS

This application is a 371 of PCT/US98/23386, filed Sep. 3, 1998, and claims the benefit of U.S. Provisional Application No. 60/066,198, filed Nov. 19, 1997.

FIELD OF THE INVENTION

This invention broadly relates to treatment strategies for lupus erythematosus. More specifically, the invention relates to prophylactic, ameliorative and curative drug therapies for lupus erythematosus.

BACKGROUND

Lupus erythematosus is an autoimmune disorder which may, but does not always, affect many different organ systems in an affected individual. Lupus erythematosus (hereinafter "lupus") may affect the heart, lungs, skin, joints, kidneys, nervous system, lymph gland system, blood cells and/or blood vessels. Certain forms of lupus affect only or predominantly the skin. These forms of lupus are the most visible manifestations of the disease.

The immune system of the body is a complex and elaborate mechanism of protection from foreign substances. The immune system provides resistance to foreign cells and substances (e.g., bacteria or virus) that may cause injury, as well as searching out abnormal cells (e.g., cancerous cells) within the body for destruction. The invading or abnormal cells are neutralized by the immune system humoral and cellular components including lymphocytes, antibodies, mediating (regulating such as lymphokines) systems, and effector (cytotoxic) cells. As an example. the immune system can recognize the invading or abnormal cells (antigens) within the body and produce antibodies (proteins) which attach to the recognized antigens, leading to their removal. Autoimmunity occurs when the immune system produces antibodies to normal cells in the body. This produces inflammation of normal tissue, resulting in damage and loss of function. In other instances, antibodies attach to antigens within the blood plasma to form immune complexes that may be deposited in normal tissue resulting in inflammation and damage.

Women are more susceptible to lupus than men. Over 90% of lupus patients are females aged 13–40 years. Laboratory tests for the presence of lupus include the LE Cell Test, the Anti-Nuclear Antibody Test, and the test for Anti-DNA-Antibodies. Lupus is, however, often recognized by particular clinical manifestations including: (i) arthritis (occurring in 90–95% of persons with systemic lupus), (ii) skin changes, such as a photosensitive induced "butterfly" rash across the bridge of the nose, across the cheeks and/or beneath the eyes, and/or red, raised and scaly patches, known as discoid lupus, anywhere on the body (occurring in 75–80% of persons with lupus), (iii) hematologic abnormalities, such as anemia, leukopenia, and thrombocytopenia (occurring in about 50% of persons with lupus), (iv) kidney impairment (occurring in about 50% of persons with lupus), (v) heart or lung disease, such as an irritation of the heart or lung lining causing pericarditis or pleurisy (occurring in about 30% of persons with lupus), and (vi) neuropsychiatric changes (occurring in about 10% to 20% of persons with lupus).

Etiology

Lupus erythematosus can be divided into subsets which may or may not have overlapping characteristics: discoid lupus, subacute cutaneous lupus, drug-induced lupus and systemic lupus. Patients in whom the disease seems to be confined to the skin are differentiated from those with systemic or "disseminated" involvement.

Discoid lupus, also called chronic discoid lupus or chronic cutaneous lupus produces lesions over the face, but sometimes spread more extensively across the body. The lesions are usually well circumscribed, disk-like plaques of scaling erythema, tending to clear centrally with scarring, depigmentation and atrophy. Photosensitivity is a common feature but may be absent. Roughly 80% to 90% of patients with discoid lupus lesions will not develop any signs and symptoms of systemic lupus.

Subacute cutaneous lupus produces wide spread skin lesions over the trunk and extremities of the patient. The lesions are apt to be less discrete than those of discoid lupus, more widespread, with temporary depigmentation and telangiectasia without scaring or atrophy. Loss of hair without scaring is common, and mild systemic disease, especially involving the joints, accompanied by fever and malaise are often present.

Another distinct subset of lupus is that associated with reaction to certain drugs, appropriately known as drug induced lupus. Serious organ involvement is rare and prognosis for this subset of lupus is excellent, provided the disease is recognized and the offending medication discontinued.

Systemic lupus is a chronic autoimmune disease that often has a relapsing course. The primary therapeutic approach for systemic lupus is to achieve and maintain adequate suppression of the disease with minimal drug mediated side effects. Evaluation of specific symptoms and clinical findings establish the type and extent of organ involvement and overall disease activity. There are two basic goals of drug treatment for lupus. The first goal is to reduce inflammation within the affected tissues. The second goal is to identify and suppress the specific abnormalities of the immune system that are considered responsible for tissue inflammation. The overall therapeutic plan generally groups lupus manifestations into four broad categories based on primary treatment modality used for initial treatment.

Fever, joint pain (arthralgias), arthritis, and serositis (pleurisy or pericarditis) can often be managed effectively by the administration of nonsteroidal, anti-inflammatory drugs (NSAIDs), such as aspirin, salisylates, ibuprofin, naproxen, clinoril, oxaprozin and tolmetin. The most common side-effects include gastrointestinal complaints and the potentiation of peptic ulcers. Acetaminophen derivatives can be safely taken with NSAIDs for added pain relief.

Cutaneous features of systemic lupus are usually most effectively managed with antimalarial drugs, such as hydroxychloroquine, chloroquine and quinacrine. Due to the high rate of cutaneous disease relapse and the safety of low-dose therapy, antimalarial drug is usually prescribed on an indefinite basis for patients displaying lupus skin conditions. Retinoids such as istretinoin (Acutane™) and etretinate (Acitretinz™) demonstrate beneficial results when given orally, with reduction of lesions refractory to traditional antimalarial drug therapy.

More serious organ involvement is generally treated by the administration of a corticosteroid, given orally or intravenously. Prednisone is the most commonly used oral corticosteroid. When oral administration of steroids proves ineffective, intravenous methyl prednisolone pulse therapy (high dose) is often used in the treatment of lupus nephritis and other serious non-renal manifestations, such as hemolytic anemia, central nervous system inflammation (cerebritis), life-threatening low-platelet counts, and severe pleuropericarditis. Mild androgenic compounds such as Danazol™ and dehydroepiandrosterone (DHEA) have also been used in controlling immune thrombocytopenia and severe hemolytic anemia.

DHEA has also been reported to be effective for treating various manifestations of systemic lupus, with a focus upon the reported ability of DBEA to affect the hormonal and immune systems.

Immunosuppressive drugs are a fourth group used in treatment of systemic lupus. These drugs are employed when corticosteroid therapy is ineffective or intolerable for the patient. Immunosuppressive drugs include azathirprine (Imuran™), cyclosporin A (Sandimmune™), alkylating agents (nitrogen mustards, cyclophosphamide, and chlorambucil), and methotrexate. These drugs are sometimes used in combination with corticosteroids.

The above described treatment regimens for lupus often meet with limited success. Hence, the search continues for alternative treatments for lupus.

SUMMARY OF THE INVENTION

The invention is directed to the prophylactic, ameliorative and curative treatment of lupus erythematosus by administering Δ5-androstene-3 β-ol-7,17-dione and precursors thereof which are readily metabolized in vivo to Δ5-androstene-3 β-ol-7,17-dione but essentially incapable of being metabolized to androgens, estrogens or dehydroepiandrosterone.

DETAILED DESCRIPTION OF THE INVENTION INCLUDING A BEST MODE

Lupus erythematosus can be treated by administering therapeutic amounts of Δ5-androstene-3β-ol-7,17 dione and precursors thereof which are readily metabolized in vivo to Δ5-androstene-3β-ol-7,17-dione but essentially incapable of being metabolized to androgens, estrogens or dehydroepiandrosterone, such as Δ5-androstene-3β-acetoxy-7,17 dione and other 3β esters thereof.

Such treatment can be prophylactic, ameliorative or curative in nature.

Without intending to be bound by any theory, it is believed that Δ5-androstene-3β-ol-7,17 dione is effective for preventing, ameliorating a erythematosus by modulating appropriate aspects of the aberrantly functioning immune system responsible for the onset and/or continuation of lupus erythematosus (i.e., increasing depressed and/or decreasing hyperactive aspects of the system), particularly with respect to the production of appropriate concentrations of IL-2.

Δ5-Androstene-3β-ol-7,1 7-dione

Δ5-androstene-3β-ol-7,17-dione is a derivative of dehydroepiandrosterone (DHEA) which does not appreciably stimulate, increase or otherwise enhance the production of sex hormones Δ5-androstene-3β-ol-7,17-dione is commercially available from a number of sources including Steraloids, Inc. of Wilton, New Hampshire. A number of procedures are available for synthesizing Δ5-androstene-3β-ol-7,17 dione from DHEA, with one such procedure described in U.S. Pat. No. 5,296,481.

Precursors of Δ5-androstene-3β-ol-7,17-dione, which are essentially incapable of being metabolized to androgens, estrogens or dehydroepiandrosterone, may also be usefully employed in the treatment of lupus erythematosus. Such precursors are readily metabolized in vivo to the active Δ5-androstene-3β-ol-7,17-dione. One example of such a metabolizable precursor is the commercially available Δ5-androstene-3β-acetyl-7,17-dione. The 3β-acetyl group is readily hydrolyzed in vivo by esterases located in the blood and various body tissue to produce the active Δ5-androstene-3β-ol-7,17-dione, and is believed to be less susceptible to oxidation at the manufacturing process relative to Δ5-androstene-3β-ol-7,17-dione.

Administration

Administration Route

The Δ5 Androstene-3β-acetoxy-7,17-dione can be administered by virtually any of the commonly accepted practices for the administration of pharmaceutical preparations including specifically, but not exclusively, intravenous injection, mucosal administration, oral consumption, ocular administration, subcutaneous injection, transdermal administration, etc.

Mucosal administration of Δ5 Androstene-3β-acetoxy-7, 17-dione includes such routes as buccal, endotracheal, inhalation, nasal, pharyngeal, rectal, sublingual, vaginal, etc. For administration through the buccal/inhalation /sublingual/pharyngeal/endotracheal mucosa, the steroid may be formulated as an emulsion, gum, lozenge, spray, tablet or an inclusion complex such as cyclodextrin inclusion complexes. Nasal administration is conveniently conducted through the use of a sniffing power or nasal spray. For rectal and vaginal administration the steroid may be formulated as a cream, douch, enema or suppository.

Oral consumption of the steroid may be effected by incorporating the steroid into a food or drink, or formulating the steroid into a chewable or swallowable tablet or capsule.

Ocular administration may be effected by incorporating the steroid into a solution or suspension adapted for ocular application such as drops or sprays.

Intravenous and subcutaneous administration involves incorporating the steroid into a pharmaceutically acceptable and injectable carrier.

For transdermal administration, the steroid may be conveniently incorporated into a lipophilic carrier and formulated as a topical creme or in an adhesive patch.

Dose Rate

The range of dosages and dose rates effective for achieving the desired biological properties and characteristics may be determined in accordance with standard industry practices. These ranges can be expected to differ depending upon whether the desired response is the prophylactic, ameliorative or curative treatment of lupus erythematosus, the type of lupus and the severity of symptoms.

EXPERIMENTAL

Experiment 1

Preparation of Δ5 Androstene-3β-acetoxy-7,17-dione

Step One:

Preparation of Δ5 Androstene-3-acetoxy-17-one

A suitable, three-necked, round-bottom flask equipped with an overhead stirrer, reflux condenser, solids addition funnel and 110-volt temperature controller was charged with a mixture of dichworomethane (90 ml), glacial acetic acid (150 ml), and acetic anhydride (250 ml). To the mixture was added dehydroepiandrosterone (0.20 moles) purchased from Steraloids, Inc. of Wilton, N.H. The mixture was stirred to dissolve the solid dehydroepiandrosterone, and anhydrous sodium acetate (35.0 g) added. The resulting mixture was heated at 75° C. with stirring for 3 hours to complete the reaction.

The reaction mixture was poured into one liter of water and the resulting slurry stirred at room temperature for 2 hours. The organic dichloromethane layer was separated from the aqueous layer, and the aqueous layer extracted once with 50 ml of to fresh dichloromehane. The combined organic dichloromethane extract was washed with water, saturated sodium bicarbonate solution (until neutral), and water. The resulting washed organic dichloromethane extract was evaporated under reduced pressure to a volume of 40 ml. Methanol (100 ml) was added to this concentrated extract and the resulting solid mass was cooled at 0° C. in a refrigerator for 2 hours.

The resulting solid white product was collected by vacuum filtration on a Buchner funnel and the filter cake air dried on the funnel to form a first crop of product weighing 50.5 g. The filtrate mother liquor was concentrated by evaporation under reduced pressure, and cooled at 0° C. in a refrigerator. The resulting solid white product was collected by vacuum filtration on a Buchner funnel and the filter cake air dried on the funnel to form a second crop of product weighing 10.2 g. The filtrate mother liquor from the second crop of product was diluted with water and the mixture was cooled at 0° C. in a refrigerator. The resulting solid white product was collected by vacuum filtration on a Buchner funnel and the filter cake air dried on the funnel to form a third crop of product weighing 4.2 g.

The first, second and third crops of product were combined to produce a total of 64.9 grams of Δ5 androstene-3-acetoxy-17-one.

Theoretical yield=66.1 g

First crop yield=50.5 g (76.4%)

Second crop yield=10.2 g (15.4%)

Third crop yield=4.2 g ( 6.4%)

Step Two:

Preparation of Crude Δ5 Androstene-3-acetoxy-7, 17-dione

A suitable, three-necked, round-bottom flask equipped with an overhead stirrer, reflux condenser, addition funnel, thermometer, mineral oil filled bubbler and a gas inlet tube connected to a nitrogen cylinder, was charged with acetone (3.5 L) and cyclohexane (3.5 L). 1.51 moles of the Δ5 Androstene-3-acetoxy-17-one prepared in Step One was added to the flask with stirring to dissolved the solid Δ5 Androstene-3-acetoxy-17-one. 2.48 moles of solid sodium metaperiodate and water (1.1 L) were added to the stirred solution. 14.75 moles of a 70% aqueous solution of t-butyl hydroperoxide(2.0 L) was added to the flask through the addition funnel over a one-half hour period.

Over the first hour, the reaction mixture temperature rose from 20° C. to 32° C. Tap water was added to an external cooling bath and the reaction mixture temperature returned to 20° C. The reaction mixture was constantly vigorously stirred throughout the experiment, and the reaction judged to be complete after 48 hours by TLC monitoring of the disappearance of starting material. The mixture changed from a white slurry to a light yellow slurry over the course of the reaction.

The reaction mixture was poured into a stirred ice/water mixture (12 kg ice and 8 L water). Potassium sulfite (3 L of a 45% aqueous solution) was then added to the diluted reaction mixture over 30 minutes (100 mL/min) to destroy any remaining oxidant. The diluted mixture was stirred for an additional 2 hours, with ice added as needed to maintain the mixture at 15° C.

The resulting diluted, cooled reaction mixture was transferred to a suitable container and ethyl acetate (3 L) was added to dissolve and extract the product. The resultant mixture was stirred for one-half hour and then allowed to stand so as to permit the organic and aqueous layers to separate. The aqueous layer was examined by TLC, found to contain no product, and discarded. The solids containing organic layer was transferred to a separatory funnel, washed with water (3×1.5 L), then washed with a saturated salt solution (1×1.5 L). The washed organic layer was dried over sodium sulfate (300 g), with decolorizing carbon (100 g) added. The resulting organic slurry was filtered through a ceramic Buchner funnel containing a 0.5 inch Celite pad (100 g). The filter cake was washed with ethyl acetate (2×150 ml) and the washing combined with the filtrate.

The combined organic filtrate was concentrated in vacuo to near dryness to produce an off-white semi-solid. The semi-solid was suspended in methanol (400 ml) and again concentrated in vacuo to near dryness to produce a semi-solid. The semisolid was slurried in methanol (600 ml) and the slurry stirred for 2 hours at ambient temperature. The solid product was collected by filtration on a ceramic Buchner funnel, and the solids washed with cold (5° C.) methanol (2×75 ml). The solid product was dried at 65° C. for 48 hours under high vacuum (<1 mm Hg vacuum). The process yielded 232 grams of crude solid Δ5 Androstene-3-acetoxy-7,17-dione.

Theoretical yield=521 g

Actual yield=232 g (44.5%)

Step Three:

Preparation of Purified Δ5 Androstene-3-acetoxy-7, 17-dione

METHOD A

A 500 ml round bottom flask equipped with a magnetic stirrer was charged with 25.0 grams of the crude Δ5 Androstene-3-acetoxy-7,17-dione prepared in Step Two and 300 ml of a mixture of methanol and ethyl acetate (1:1, v/v). The magnetic stirrer was activated and the slurry stirred at room temperature until the crude Δ5 Androstene-3-acetoxy-7,17-dione was completely dissolved in the solvent mixture to form a first solution. A freshly prepared 10% aqueous solution of sodium bicarbonate (25 ml) was added over 10 minutes to the reaction mixture. The resulting milky mass was stirred at room temperature for 2.5 hours.

The reaction mixture was concentrated at room temperature under reduced pressure to 100 ml volume. The concentrated reaction mixture was diluted with 200 ml of ice water and stirred for 30 minutes at 0–5° C. The precipitated solids were collected on a ceramic Buchner funnel, and the aqueous filtrate reserved for additional product recovery. The solids on the funnel were washed with water (until neutral), and methanol (2×30 ml), with the methanol washing also reserved for product recovery. The first crop of solids was dried overnight under vacuum to give 18.0 g of purified product.

The aqueous filtrate from the first crop of solids was extracted with ethyl acetate (100 ml), and the separated organic extract was washed with water. The solvent of the washed extract was removed under reduced pressure to produce a solid product. This solid product was dissolved in the methanol washing from the first crop of solids, and the solution concentrated to 30 ml volume. Upon cooling the concentrate, a solid precipitate product formed which was collected by vacuum filtration. The second crop of solids was air dried to give 5.2 g of purified product.

The mother liquor filtrate from the second crop of solids was diluted with water and cooled. The resulting white solid precipitate was collected by vacuum filtration, and dried overnight at room temperature to give a third crop of 1.0 g of purified product.

The process yielded a total of 24.2 grams of purified solid Δ5 Androstene-3-acetoxy-7,17-dione.

Theoretical recovery=25.0 g

Actual recovery=24.2 g (96.8%)

METHOD B

A suitable round bottom flask equipped with a magnetic stirrer was charged with 1.0 gram of the crude Δ5 Androstene-3-acetoxy-7,17-dione prepared in Step Two and 10 ml of acetone. The magnetic stirrer was activated and the slurry was stirred at room temperature until the crude Δ5 Androstene-3-acetoxy-7,17-dione was completely dissolved in the acetone. To this solution was added 2.0 g of aluminum oxide basic. The resulting slurry was stirred at room temperature for 1 hour, then filtered through a bed of Celite. The collected solids and Celite bed were washed once with 5 ml of acetone, and the washing combined with the filtrate. The combined filtrate was evaporated to near dryness under reduced pressure to produce a solid product. The solid product was dissolved in a mixture of methanol and isopropyl ether (8:2, v/v) with heating. This solution was cooled at −5° C. for 30 minutes, resulting in precipitation of a white product. The precipitated solid was collected by vacuum filtration and air dried to give 0.9 grams of purified solid Δ5 androstene-3-acetoxy-7,17-dione.

Theoretical recovery=1.0 g actual recovery=0.9 g (90.0%)

We claim:

1. A treatment method comprising treating a patient having an autoimmune disorder with an effective autoimmune disorder ameliorative amount of a steroid selected from the group consisting of Δ5-androstene-3β-ol-7,17-dione and metabolizable precursors thereof incapable of being metabolized to androgens, estrogens or dehydroepiandrosterone.

2. The treatment method of claim 1 wherein said steroid is selected from the group consisting of Δ5-androstene-3β-ol-7,17-dione and Δ5-androstene-3β-acetoxyol-7,17-dione.

3. The treatment method of either one of claims 1 and 2 wherein said autoimmune disorder is lupus erythematosus.

4. The treatment method of claim 3 wherein said autoimmune disorder is systemic lupus erythematosus.

5. The treatment method of claim 3 wherein said autoimmune disorder is lupus erythematosus-related tissue inflammation.

6. A treatment method comprising treating a patient diagnosed with an autoimmune disorder with an effective autoimmune disorder preventative amount of a steroid selected from the group consisting of Δ5-androstene-3β-ol-7,17-dione and metabolizable precursors thereof incapable of being metabolized to androgens, estrogens or dehydroepiandrosterone.

7. The treatment method of claim 6 wherein said steroid is selected from the group consisting of Δ5-androstene-3β-ol-7,17-dione and Δ5-androstene-3β-acetoxyol-7,17-dione.

8. The treatment method of either one of claim 6 and 7 wherein said autoimmune disorder is lupus erythematosus.

9. The treatment method of claim 1, wherein said patient is a human.

10. The treatment method of claim 1, wherein said autoimmune disease is in remission.

11. The treatment method of claim 2, wherein said patient is a human.

12. The treatment method of claim 2, wherein said autoimmune disease is in remission.

13. The treatment method of claim 2 wherein said autoimmune disorder is lupus erythematosus-related tissue inflammation.

14. The treatment method of claim 3, wherein said patient is a human.

15. The treatment method of claim 3, wherein said autoimmune disease is in remission.

16. The treatment method of claim 3, wherein said autoimmune disease is selected from the group consisting of discoid lupus erythematosus, subacute cutaneous lupus erythematosus, drug-induced lupus erythematosus, and systemic lupus erythematosus.

17. The treatment method of claim 3, wherein said treatment ameliorates a clinical manifestation selected from the group consisting of lupus erythematosus-related arthritis, lupus erythematosus-related skin changes, lupus erythematosus-related hematologic abnormalities, lupus erythematosus-related kidney impairment, lupus erythematosus-related heart or lung disease, and lupus erythematosus-related neuropsychiatric changes.

18. The treatment method of claim 6, wherein said patient is a human.

19. The treatment method of claim 6, wherein said autoimmune disease is in remission.

20. The treatment method of claim 7, wherein said patient is a human.

21. The treatment method of claim 7, wherein said autoimmune disease is in remission.

22. The treatment method of claim 8, wherein said autoimmune disorder is systemic lupus erythematosus.

23. The treatment method of claim 8, wherein said patient is a human.

24. The treatment method of claim 8, wherein said autoimmune disease is in remission.

25. The treatment method of claim 8, wherein said autoimmune disease is selected from the group consisting of discoid lupus erythematosus, subacute cutaneous lupus erythematosus, drug-induced lupus erythematosus, and systemic lupus erythematosus.

26. The treatment method of claim 8, wherein said treatment prevents a clinical manifestation selected from the group consisting of lupus erythematosus-related arthritis, lupus erythematosus-related skin changes, lupus erythematosus-related hematologic abnormalities, lupus erythematosus-related kidney impairment, lupus erythematosus-related heart or lung disease, and lupus erythematosus-related neuropsychiatric changes.

* * * * *